United States Patent [19]

Berges

[11] 4,107,173

[45] Aug. 15, 1978

[54] 3-SULFOMETHYL-1,2,4-TRIAZOLE-5-THIOL AND ITS ALKALI METAL SALTS

[75] Inventor: David A. Berges, Wayne, Pa.

[73] Assignee: SmithKline Corporation, Philadelphia, Pa.

[21] Appl. No.: 856,447

[22] Filed: Dec. 1, 1977

Related U.S. Application Data

[62] Division of Ser. No. 726,377, Sep. 24, 1976.

[51] Int. Cl.$^2$ ............................................. C07D 249/12
[52] U.S. Cl. .............................. 260/308 R; 260/308 C
[58] Field of Search ........................ 260/308 R, 308 C

[56] References Cited

FOREIGN PATENT DOCUMENTS 2,412,564  10/1974  Fed. Rep. of Germany ...... 260/308 R

*Primary Examiner*—Alton D. Rollins
*Attorney, Agent, or Firm*—William H. Edgerton

[57] ABSTRACT

New semisynthetic cephalosporins characterized by having structures with a 3-sulfomethyl-1,2,4-triazol-5-ylthiomethyl group at position 3. Exemplary is the antibacterially effective 7-D-mandelamido-3-(3-sulfomethyl-1,2,4-triazol-5-ylthiomethyl)-3-cephem-4-carboxylic acid disodium salt.

3 Claims, No Drawings

3-SULFOMETHYL-1,2,4-TRIAZOLE-5-THIOL AND ITS ALKALI METAL SALTS

This is a division of application Ser. No. 726,377, filed Sept. 24, 1976.

This invention relates to a new series of cephalosporin compounds having antibacterial activity and to intermediates useful for preparing them. The structures of the new compounds are characterized by having at the 3-position a sulfoalkyl substituted 1,2,4-triazol group.

Exemplary of the compounds of this invention are those represented by the following structural formula:

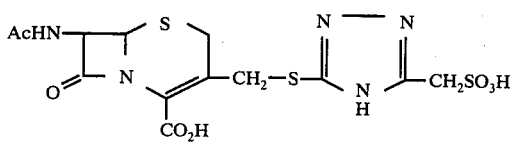

in which Ac represents a pharmaceutically acceptable acyl group known to be of utility as a substitutent on the 7-amino group in the structures of known or prior art cephalosporins or on the 6-amino group in the structures of known or prior art penicillins with the provision that Ac does not contain a substituted or unsubstituted thiazole (or thiazoline) moiety.

Representative acyl substituents are:

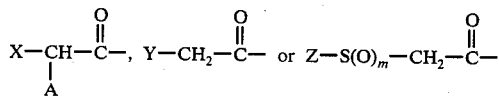

wherein:

X is thienyl, furyl, phenyl or phenyl monosubstituted with hydroxy, hydroxymethyl, formamido or ureido;

A is $NH_2$, OH, COOH, $SO_3H$, formyloxy or, when the α-C-hydrogen is absent, methoxyimino;

Y is cyano, sydnone, pyridone, thienyl, o-aminomethylphenyl, phenyl or tetrazolyl;

Z is methyl, trifluoromethyl, trifluoroethyl, pyridyl or cyanomethyl; and m is zero to two.

Each of the three partial structures above represent subgeneric groups of compounds covered by this invention.

Representative 7-acylamino substituents of the compounds of Formula I are listed below:

α-hydroxyphenylacetamido
α-aminophenylacetamido
α-amino-4-hydroxyphenylacetamido
trifluoromethylthioacetamido
2,2,2-trifluoroethylsulfinylacetamido
2,2,2-trifluoroethylthioacetamido
cyanoacetamido
α-carboxythienylacetamido
α-carboxyphenylacetamido
α-sulfophenylacetamido
methylsulfonylacetamido
cyanomethylthioacetamido
3-sydnoneacetamido
1-tetrazolylacetamido
2-thienylacetamido
syn-2-methoxyimino-2-α-furylacetamido
4-pyridylthioacetamido
o-aminomethylphenylacetamido Others together with N-acylation procedures may be found in Cephalosporins and Penicillins, Flynn, Academic Press, 1972; U.S. Pat. Nos. 2,721,196 and 3,953,424; Belgian Pat. No. 832,725; German Pat. Nos. 2,127,285 and 2,406,165.

It will be recognized that the 4-carboxylic acid group of the compounds of Formula I may be readily esterified by methods well known to the art. These esters include, for example, simple alkyl and aryl esters as well as esters which are easily cleaved, within the body, to the parent acid such as indanyl, pivaloyloxymethyl, acetoxymethyl, propionyloxymethyl, glycyloxymethyl, phenylglycyloxymethyl and thienylglycyloxymethyl esters and others. Of course, when A is COOH, this group may be similarly esterified. All such ester derivatives are included within the scope of this invention.

Also covered in this invention are the pharmaceutically acceptable, nontoxic derivatives of the compounds of Formula I from which they derive utility: the salts, as stated above, easily split ester or ether derivatives of either a carboxy or hydroxy function, amide derivatives at an amino radical such as in a 7-glycylamino group as the furyl-, pyranyl-, oxolanyl- or oxiranyl-carbonyl amides (i.e. Belgian Pat. No. 835,295), the solvates such as hydrates, glycolates or alcoholates. As examples of these, one skilled in the art would be able to prepare and use the alkali metal salts such as the sodium or potassium salts (for example using sodium or potassium 2-ethyl hexanoate), ammonium salts, organic amine salts such as those with procaine or dibenzylethylenediamine.

Other known cephalosporin modifications can be made by known synthetic procedures such as introduction of an α-methoxy group at position 7, preferably at the stage of the 7-aminocephalosporanic acid reactants disclosed below (IV), prior to N-acylation. Optical isomers are also possible such as with the mandeloyl or phenyl glycyl substituents at 7. The D-forms of these subgeneric groups are preferred.

The compounds of this invention are most conveniently prepared by a displacement of the acetoxy group of a known 7-acylaminocephalosporanic acid (II) by 3-sulfomethyl-1,2,4-triazole-5-thiol (III). Alternatively a similar displacement with the thiol can be run on 7-aminocephalosporanic acid to give 7-amino-3-(3-sulfomethyl-1,2,4-triazol-5-ylthiomethyl)-3-cephem-4-carboxylic acid (IV) which may then be N-acylated as known to the art as described above. Suitable protective groups may be used in either method as is known to the art (see "Protective Groups in Organic Chemistry". J.F.W. McOmie, Plenum Press, 1973, Chapters 2 and 3 for use of amino, carboxy, sulfo or hydroxyl protective groups).

For example, the t-butyl (for COOH) or t-butoxycarbonyl (for $NH_2$) groups are easily removed by treatment with trifluoroacetic acid.

The compounds of Formula I have antibacterial activity against either Gram positive or Gram negative bacteria with minimum inhibitory concentrations (MIC's) in vitro from 0.4 to 200 μg/ml. Test results for 7-D-(—)-mandelamido-3-(3-sulfomethyl-1,2,4-triazol-5-ylthiomethyl)-3-cephem-4-carboxylic acid, disodium salt, dihydrate (A) are:

|  | A | Cefazolin | Cephalothin |
|---|---|---|---|
| S. aureus HH 127 | 3.1 | 0.4 | 0.2 |
| S. aureus SK 23390 | 3.1 (1.6) | 0.2 | 0.2 (0.1) |
| S aureus villaluz SK 70390 | >200 | 200 (100) | 50 |
| Strep. Faecalis HH 34358 | 200 | 6.3 | 12.5 |
| E. coli SK 12140 | 0.8 (1.6) | 0.8 | 6.3 (3.1) |
| E. coli HH 33779 | 1.6 | 1.6 (0.8) | 6.3 |
| Kleb. pneumo. SK 4200 | 0.8 | 1.6 | 1.6 (3.1) |
| Kleb. pneumo. SK 1200 | 0.4 (0.8) | 0.4 (0.8) | 1.6 (3.1) |
| Salmonella ATCC 12176 | 0.8 | 0.8 | 0.8 (1.6) |
| Pseudo. aeru. HH 63 | >200 | >200 | >200 |
| Serratia marc. ATCC 13880 | 25 | >200 | >200 |
| Proteus morgani 179 | 25 (12.5) | 200 | >200 |
| Entero. aergo. ATCC 13048 | 3.1 | 1.6 | 12.5 |
| Entero. cloacae HH 31254 | 1.6 | 0.8 | 6.3 |
| Proteus mirabilis PN-444 | 0.8 | 3.1 | 3.1 |

Compound A gave an $ED_{50}$ in mice of 1.02 mg/kg (s.c.) and 26 mg/kg (p.o.) against *E. coli*, 1.02 mg/kg against *Kleb. pneumo.* (s.c.). Cephalexin gives comparable values of 12.5 (s.c.) and 25 (p.o.) against *E. coli*. Cephaloridine gives a comparable value of 6.25 (s.c.) against *Kleb. pneumo.*

Pharmaceutical compositions having antibacterial activity which comprise a pharmaceutical carrier containing an active but nontoxic quantity of a compound of Formula I as well as methods of combatting bacterial infections by administering such a composition to an infected animal or human host in a nontoxic amount sufficient to combat such infections are also objects of this invention. The administration may be orally or by parenteral injection such as subcutaneously, intramuscularly or intravenously. The injection of suitably prepared sterile solutions or suspensions containing an effective, nontoxic amount of the new cephalosporin compound is the preferred route of administration.

The compounds of Formula I are formulated and administered in the same manner as other prior art cephalosporins such as cephazolin or cephalothin. The dosage regimen comprises administration, preferably by injection, of an active but nontoxic quantity of a compound of Formula I selected from the dosage unit range of from about 250 mg to 600 mg with the total daily dosage regimen being from about 750 mg to 6 g. The compounds as their sodium or potassium salts are very water soluble compared with non-sulfo congeners in the art. The precise dosages are dependent upon the age and weight of the subject and on the susceptibility of the infection being treated to each individual. These can be determined by those skilled in the art based on the data disclosed herein compared with that available to the art attained with the known cephalosporins outlined herebefore.

The following examples illustrate the invention but are not to be construed as limiting the scope thereof. Temperatures are in degrees Centigrade (°C.) unless otherwise stated.

EXAMPLE 1

A mixture of 15.8 g (0.1 mol) of potassium sulfite in 10 ml of water and 12.2 g (0.1 mol) ethyl chloroacetate in 50 ml of ethanol was warmed at gentle reflux for 4 hours then stirred at room temperature overnight. The solid was collected, washed with ethanol and air dried to give potassium ethoxycarbonylmethane sulfonate (Beilstein 4, II, 532), m.p. 213°–238°.

A mixture of 17.3 g (0.84 mol) of the methanesulfonate in 840 ml of water with 37.8 g (37.8 ml, 1.18 mol) of hydrazine was heated at reflux overnight. The solution was evaporated to a syrup which began to crystallize partially. The syrup was dissolved in 300 ml warm water, filtered, and methanol was added to the filtrate. Scratching gave crystals which were the desired potassium hydrazinocarbonylmethanesulfonate.

The hydrazide (19.2 g, 0.1 mole) and 16.5 (0.1 mol) of the carbamodithioic acid anhydrosulfide with ethyl carbonate were mixed with 250 ml of 1:1 water-ethanol and heated at reflux overnight. The mixture was taken to pH 10-11 with 10% aqueous sodium hydroxide and heated on a steam bath for 1 hour. After cooling overnight the solution was evaporated to dryness. The residue was taken up in warm dimethylformamide. The insoluble material was collected. The filtrate was evaporated to a heavy oil which was treated with methanol to give a solid. A second crop was also obtained to give, with m.p. 318.5°–319.5°, the hydrated sodium salt of 5-mercapto-1,2,4-triazole-3-methane sulfonic acid or 3-sulfomethyl-1,2,4-triazole-5-thiol. Treatment of an aqueous solution of the salt with a strongly acidic ion-exchange resin followed by lyophilization gives the acid. This acid and its alkali metal salts such as the sodium or potassium salts are important new intermediates.

A mixture of 6.4 g (0.015 mol) of 7-D-(−)-mandelamidocephalosporanic acid and 2.21 (0.01 mol) of 3-sulfomethyl-1,2,4-triazol-5-thiol sodium salt one quarter hydrate in 75 ml of water was taken to pH 6.8 with solid sodium bicarbonate. The solution was stirred at 67° for 6 hours. The mixture was layered with ethyl acetate then acidified to pH 1.5 with 6N sulfuric acid. The layers were separated. The aqueous layer was reextracted with ethyl acetate. The aqueous phase was adjusted to pH 6.8 for overnight storage then taken to pH 1.8 prior to passing over an XAD-7 resin column ( a crosslinked polymer of acrylic esters with an average pore diameter of 80 Å). Elution with water gave a series of product-containing eluates which were combined and evaporated. The syrup left after evaporation was taken up in 75 ml of water and lyophilized.

The lyophilizate was then taken up in 12.5 ml. of methanol. After filtration, the filtrate was evaporated to half volume then treated with diethyl ester to precipitate a solid which was dissolved in water and lyophilized to give a fluffy white solid, 7-D-(−)-mandelamido-3-(3-sulfomethyl-1,2,4-triazol-5-thiomethyl)-3-cephem-4-carboxylic acid disodium salt dihydrate.

Anal. Calcd. C, 36.71; H, 3.40; N, 11.25. Found: C, 36.89; H, 3.83; N, 11.32.

EXAMPLE 2

A mixture of 5.22 g (10.0 mmol) of 7-(D-α-t-butoxycarbonylamino-4-hydroxyphenylacetamido)cephalosporanic acid and an excess (15.0 mmol) of 3-sulfomethyl-1,2,4-triazol-5-thiol in 75 ml of pH 6.4 phosphate buffer solution is treated with sufficient sodium bicarbonate to give a pH of 6.4. The mixture is heated at 70° for 3 hours, cooled, acidified with dilute hydrochloric acid to pH 2 and extracted with ethyl acetate. The aqueous solution is adjusted to pH 7.0 with sodium bicarbonate and added to a XAD-7 resin column. Elution with water and then methanol followed by evaporation of the product containing fractions gives the t-boc derivative of the desired compound. This derivative is stirred at 25° C. with 25 ml of trifluoroacetic acid and 25 ml of 1,3-dimethoxybenzene for 2 hours. The mixture is evaporated to dryness, ether added to the residue and the precipitated salt collected. This is dissolved in water and one molecular equivalent of sodium bicarbonate is added. The solution is lyophilized and then tritrated with acetone to give 7-(D-α-amino-4-hydroxyphenylacetamido)-3-(3-sulfomethyl-1,2,4-triazol-5-ylthiomethyl)-3-cephem-4-carboxylic acid. Similar treatment of the t-boc derivatives of the 7-DL-(α-aminophenylacetamidocephalosporanic acid gives the corresponding 7-DL-(α-aminophenylacetamido)-3-(3-sulfomethyl-1,2,4-triazol-5-ylthiomethyl)-3-cephem-4-carboxylic acid.

EXAMPLE 3

A mixture of an excess (12.2 mmol) of 3-sulfomethyl-1,2,4-triazol-5-thiol, 32.5 mmol of sodium bicarbonate and 8.1 mmol of 7-trifluoromethylthioacetamidocephalosporanic acid in 50 ml of water is stirred at 70° for 5 hours. The reaction mixture is cooled and passed over XAD-2 resin with water and methanol as eluants. The methanol eluants were evaporated to dryness to give a residue which is dissolved in a small amount of water and lyophilized to give 7-trifluoromethylthioacetamido-3-(3-sulfomethyl-1,2,4-triazol-5-ylthiomethyl)-3-cephem-4-carboxylic acid disodium salt. Substituting 7-(2-thienylacetamidocephalosporanic acid gives 7-(2-thienylacetamido)-3-(3-sulfomethyl-1,2,4-triazol-5-ylthiomethyl)-3-cephem-4-carboxylic acid disodium salt.

Stoichiometric quantities of cephalosporanic acids having the individual 7-acylamino substituent listed hereabove may be substituted in Examples 1–3 with variations which will be obvious to those skilled in this art.

EXAMPLE 4

An injectable pharmaceutical composition is formed by adding sterile saline solution (2 ml) to 500 mg of the product of Example 1. This material is injected parenterally four times daily to a human patient infected with susceptible bacteria. Other compounds of this invention may be similarly used.

What is claimed is:
1. 3-Sulfomethyl-1,2,4-triazol-5-thiol and its alkali metal salts.
2. The compound of claim 1 being 3-sulfomethyl-1,2,4-triazol-5-thiol.
3. The compound of claim 1 being the sodium salt.

* * * * *

Disclaimer 4,107,173.—*David A. Berges*, Wayne, Pa. 3-SULFOMETHYL-1, 2, 4-TRIAZOLE-5-THIOL AND ITS ALKALI METAL SALTS. Patent dated Aug. 15, 1978. Disclaimer filed Feb. 11, 1981, by the assignee, *SmithKline Corp.*

Hereby enters this disclaimer to claims 1, 2 and 3 of said patent.

[*Official Gazette May 12, 1981.*]